(12) United States Patent
Binetti et al.

(10) Patent No.: US 8,617,519 B2
(45) Date of Patent: Dec. 31, 2013

(54) INJECTABLE CROSS-LINKED HYDROGELS FOR BIOMATERIAL APPLICATIONS

(75) Inventors: Valerie R. Binetti, Havertown, PA (US); Kristin B. Kita, West Chester, PA (US); Garland W. Fussell, West Chester, PA (US); Anthony M. Lowman, Wallingford, PA (US); Michele S. Marcolongo, Aston, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 185 days.

(21) Appl. No.: 13/177,613

(22) Filed: Jul. 7, 2011

(65) Prior Publication Data

US 2013/0012913 A1 Jan. 10, 2013

(51) Int. Cl.
*A61K 49/00* (2006.01)
*A61M 5/00* (2006.01)
*A61L 27/18* (2006.01)
*B29C 45/00* (2006.01)
*C08L 29/04* (2006.01)

(52) U.S. Cl.
USPC .......... 424/9.1; 264/328.2; 523/113; 604/500

(58) Field of Classification Search
USPC .......... 424/9.1; 264/328.1; 523/113; 604/500
See application file for complete search history.

(56) References Cited

U.S. PATENT DOCUMENTS

| | | | |
|---|---|---|---|
| 5,047,055 A | 9/1991 | Bao et al. | |
| 5,941,909 A | 8/1999 | Purkait | |
| 7,214,245 B1 | 5/2007 | Marcolongo et al. | |
| 7,235,592 B2 | 6/2007 | Muratoglu et al. | |
| 7,708,979 B2 | 5/2010 | Lowman et al. | |
| 2003/0129730 A1 | 7/2003 | Chenite et al. | |
| 2005/0271725 A1 | 12/2005 | Kuribayashi et al. | |
| 2007/0275030 A1 | 11/2007 | Muratoglu et al. | |

FOREIGN PATENT DOCUMENTS

WO 2009146331 12/2009

OTHER PUBLICATIONS

Derwent-Acc-No. 1994-132195 abstracting JP 06080890 Takashima Mar. 22, 1994 3 pages.*
Ruiz et al. (Journal of Applied Polymer Science 2003,88,3026-3031).*
Martens, P., et al., Characterization of hydrogels formed from acrylate modified poly(vinyl alcohol) macromers, Polymer, vol. 41 (2000), pp. 7715-7722.
Peppas, et al., Crosslinked Poly(vinyl Alcohol) Hydrogels as Swollen Elastic Networks, Journal of Applied Polymer Science, vol. 21 (1977), pp. 1763-1770.
Bader, R., et al., Rheological characterization of photopolymerized poly(vinyl alsohol) hydrogels for potential use in nucleus pulposus replacement, Journal of Biomedical Mat. Res. Part A, www.interscience.wiley.com, DOI: 10.1002.jbm.a.31637, 2008.

(Continued)

*Primary Examiner* — Ernst Arnold
(74) *Attorney, Agent, or Firm* — Stradley Ronon Stevens & Young, LLP

(57) ABSTRACT

An injectable hydrogel composition comprising: water; and poly(vinyl alcohol) chemically cross-linked with a second polymer to form a cross-linked resin, wherein the second polymer is selected from the group consisting of: a polyhydric alcohol compound, a polyvalent epoxy compound, a polyvalent amine compound, a dialdehyde compound, a diisocyanate compound, and mixtures thereof, wherein the cross-linked resin has a degree of cross-linking of from about 0.0001 mol/mL to about 0.002 mol/mL, and wherein the hydrogel is flowable when heated above its melting point.

21 Claims, 6 Drawing Sheets

(56) References Cited

OTHER PUBLICATIONS

Bao, Q., et al., Prosthetic Disc Replacement: The Future?, Clin. Orthopaedics and Related Research, No. 394, pp. 139-145, 2002.

Halloran, D., et al., An injectable cross-linked scaffold for nucleus pulposus regeneration, Biomaterials, vol. 29 (2008), pp. 438-447.

Joshi, et al., Functional compressive mechanics of a PVA/PVP nucleus pulposus replacement, Biomaterials, vol. 27 (2006), pp. 176-184.

Leone, G, et al., PVA/STMP based hydrogels as potential substitutes of human vitreous, J. Mater Sci: Mater Med, vol. 21 (2010), pp. 2491-2500.

Lowman, A, et al., Hydrogels, John Wiley & Sons, 1999, pp. 397-406.

Mow, V., et al., Biphasic Creep and Stress Relaxation of Articular Cartilage in Compression: Theory and Experiments, Journal of Biomechanical Eng, vol. 102, Feb. 1980, pp. 73-84.

Peppas, N., et al., Semicrystalline poly(vinyl alcohol) films and their blends with poly(acrylic acid) and poly(ethylene glycol) for drug delivery applications, J. Drug Del. Sci. Tech, 14 (4), 2004, pp. 291-297.

Proctor, C.S., et al., Material Properties of the Normal Medial Bovine Meniscus, Journal of Orthopaedic Research, vol. 7 (1989), pp. 771-782.

The Effect of Dehydration History on PVA/PVP Hudrogels for Nucleus Pulposus Replacement, Thomas, J., et al., Dept. of Materials Science and Eng. and Dept. of Chem. Eng., Drexel Univ., Apr. 24, 2003, rev. Jun. 20, 2003.

Thesis of Abhijeet Bhaskar Joshi dated Feb. 2004, Mechanical Behavior of the Human Lumbar Invertebral Disc with Polymeric Hydrogel Nucleus Implant: An Experimental and Finite Element Study.

Thomas, J., et al., Novel associated hydrogels for nucleus pulposus replacement, Dept. of Materials Science and Eng. and Dept. of Chem. Eng., Drexel Univ., Jun. 17, 2002, rev. Mar. 19, 2003.

Urgan, J.P.G., et al., Swelling Pressure of the Lumbar Intervertebral Discs: Influence of Age, Spinal Level, Composition, and Degeneration, Univ Lab. of Phys., Oxford Univ, Bone and Joint Research Unit, London Hosp Med. College, Oct. 20, 1986, rev. Aug. 30, 1987.

\* cited by examiner

INJECTABLE CROSS-LINKED HYDROGELS FOR BIOMATERIAL APPLICATIONS

BACKGROUND OF THE INVENTION

The present invention relates to a cross-linked hydrogel composition that is flowable when heated to above its melting point and an elastic solid at physiological body temperature and below. The present invention is also directed to the use of such hydrogels as a biomaterial to repair or supplement body tissue and, in particular, an intervertebral disc nucleous.

Hydrogels are water-swellable or water-swollen materials whose structure is typically defined by a crosslinked or interpenetrating network of hydrophilic homopolymers or copolymers. The hydrophilic homopolymers or copolymers can be water-soluble in free form, but in a hydrogel they may be rendered insoluble generally due to the presence of covalent, ionic, or physical crosslinks. In the case of physical crosslinking, the linkages can take the form of entanglements, crystallites, or hydrogen-bonded structures. The crosslinks in a hydrogel provide structure and physical integrity to the polymeric network.

Poly(vinyl alcohol) ("PVA") hydrogels have been used for biomedical applications, including nucleus pulposus and soft tissue replacements or repair. For example, U.S. Pat. No. 5,047,055 discloses the use of 100% semi-crystalline PVA for nucleus pulposus replacement. Another PVA hydrogel for nucleus replacement is disclosed in U.S. Pat. No. 7,214,245, which describes the addition of poly(vinyl pyrrolidone) ("PVP") to the PVA hydrogel for stabilization. The addition of PVP was found to reduce PVA degradation in the body, which is the result of melting out of smaller crystallites over time. This degradation can reduce the hydrogel's mechanical properties in addition to leaching molecules into the surrounding physiological environment. International Publication Number WO 2009/146331 A1 discloses an injectable nucleus pulposus replacement consisting of PVA/PVP and PEG. This hydrogel consists of physical cross-links, which do not offer advantages such as stability or property tailoring that is typical of chemical cross-linking.

Chemical cross-linking of PVA can help achieve the desired mechanical and swelling properties, in addition to further reducing the degradation of PVA due to the use of covalent bonds giving network structure. A chemically cross-linked network is not as susceptible to the melting out of the crystallites, as is a physically cross-linked network. U.S. Pat. No. 5,941,909 discloses the use of PVA chemically cross-linked with glutaraldehyde for filling material for soft tissue implant prostheses and implants. U.S. patent application Ser. No. 12/747,411 describes the use of cross-linking polyethyleneimine with a hydrogen-bonding polymer such as PVA. These hydrogel networks have to be injected immediately after mixing, which is an added complication for the surgeon performing the nucleus pulposus replacement. Another chemically cross-linked PVA hydrogel, used for human vitreous substitutes, PVA is cross-linked with trisodium trimetaphosphate. This cross-linked material has a modulus of 3.9 to 1290 Pa, which is sufficient for human vitreous substitutes but is too low for nucleus pulposus replacement and other soft tissues. PVA has also been cross-linked with glycidyl methacrylate with the use of a photoinitiator 2-hydroxy-1-[4-(2-hydroxyethoxy)phenyl]-2-methyl-1-propanone for nucleus replacement. The cross-linked nucleus replacement is not an injectable material. Another chemically cross-linked material is an injectable cross-linked scaffold for nucleus pulposus regeneration. This scaffold is composed of atelocollagen type II, hyaluronan, aggrecan and crosslinked with mTGase (see, e.g., Halloran, D. O., et al., *An injectable cross-linked scaffold for nucleus pulposus regeneration*. Biomaterials, 2008. 29: p. 438-447). It is a significant drawback, however, that this scaffold is not suitable for total nucleus replacement because it has a low modulus (250-1300 Pa).

Accordingly, there is a need in the art for a cross-linked hydrogel that is injectable and does not suffer from the aforementioned drawbacks.

BRIEF SUMMARY OF THE INVENTION

The present invention satisfies this need by providing an injectable hydrogel composition comprising: water; and poly(vinyl alcohol) chemically cross-linked with a second polymer to form a cross-linked resin, wherein the second polymer is selected from the group consisting of: a polyhydric alcohol compound, a polyvalent epoxy compound, a polyvalent amine compound, a dialdehyde compound, a diisocyanate compound, and mixtures thereof, wherein the cross-linked resin has a degree of cross-linking of from about 0.0001 mol/mL to about 0.002 mol/mL, and wherein the hydrogel is flowable when heated above its melting point.

In another aspect, the present invention provides a process for making a hydrogel composition comprising water; and poly(vinyl alcohol) chemically cross-linked with a second polymer to form a cross-linked resin, wherein the second polymer is selected from the group consisting of: a polyhydric alcohol compound, a polyvalent epoxy compound, a polyvalent amine compound, a dialdehyde compound, a diisocyanate compound, and mixtures thereof, wherein the cross-linked resin has a degree of cross-linking of from about 0.0001 mol/mL to about 0.002 mol/mL, and wherein the hydrogel is flowable when heated above its melting point, the process comprising the steps of: forming an aqueous solution of poly(vinyl alcohol) and water in a sealed pressurized container; heating the aqueous solution to a temperature of from about 90° C. to about 125° C.; cooling the aqueous solution to a temperature of from about 70° C. to about 80° C.; adding the second polymer and a catalyst to the aqueous solution, wherein the catalyst is selected from the group consisting of: an acid and a base; cooling the solution to ambient temperature; chemically cross-linking the PVA and the second polymer; and holding the solution at ambient temperature for a period of from about 1 to about 48 hours to allow for the completion of chemical cross-linking and formation of a hydrogel composition that is flowable when heated above its melting point.

In yet another aspect, the present invention provides a process for forming an intervertebral implant directly in a patient, the process comprising the steps of: heating a hydrogel composition to above its melting point such that the composition is flowable, the hydrogel composition comprising: water; and poly(vinyl alcohol) chemically cross-linked with a second polymer to form a cross-linked resin, wherein the second polymer is selected from the group consisting of: a polyhydric alcohol compound, a polyvalent epoxy compound, a polyvalent amine compound, a dialdehyde compound, a diisocyanate compound, and mixtures thereof, wherein the cross-linked resin has a degree of cross-linking of from about 0.0001 mol/mL to about 0.002 mol/mL, and wherein the hydrogel is flowable when heated above its melting point; and injecting the flowable hydrogel composition into a cavity of an intervertebral disc of a patient who has had at least a portion of nucleus pulposus tissue removed from the intervertebral disc.

In still another aspect, the present invention provides a process for forming an intervertebral implant, the process comprising the steps of: heating a hydrogel composition to above its melting point such that the composition is flowable, the hydrogel composition comprising: water; and poly(vinyl alcohol) chemically cross-linked with a second polymer to form a cross-linked resin, wherein the second polymer is selected from the group consisting of: a polyhydric alcohol compound, a polyvalent epoxy compound, a polyvalent amine compound, a dialdehyde compound, a diisocyanate compound, and mixtures thereof, wherein the cross-linked resin has a degree of cross-linking of from about 0.0001 mol/mL to about 0.002 mol/mL, and wherein the hydrogel is flowable when heated above its melting point; injecting the flowable hydrogel composition into a mold; and cooling the hydrogel composition.

Other aspects, features and embodiments of the invention will be more fully apparent from the ensuing disclosure and appended claims.

BRIEF DESCRIPTION OF THE DRAWINGS

The foregoing and other objects, advantages and features of the invention, and the manner in which the same are accomplished, will become more readily apparent upon consideration of the following detailed description of the invention taken in conjunction with the accompanying Figures, which illustrate preferred and exemplary embodiments, wherein.

DETAILED DESCRIPTION OF THE INVENTION

Figure 1:
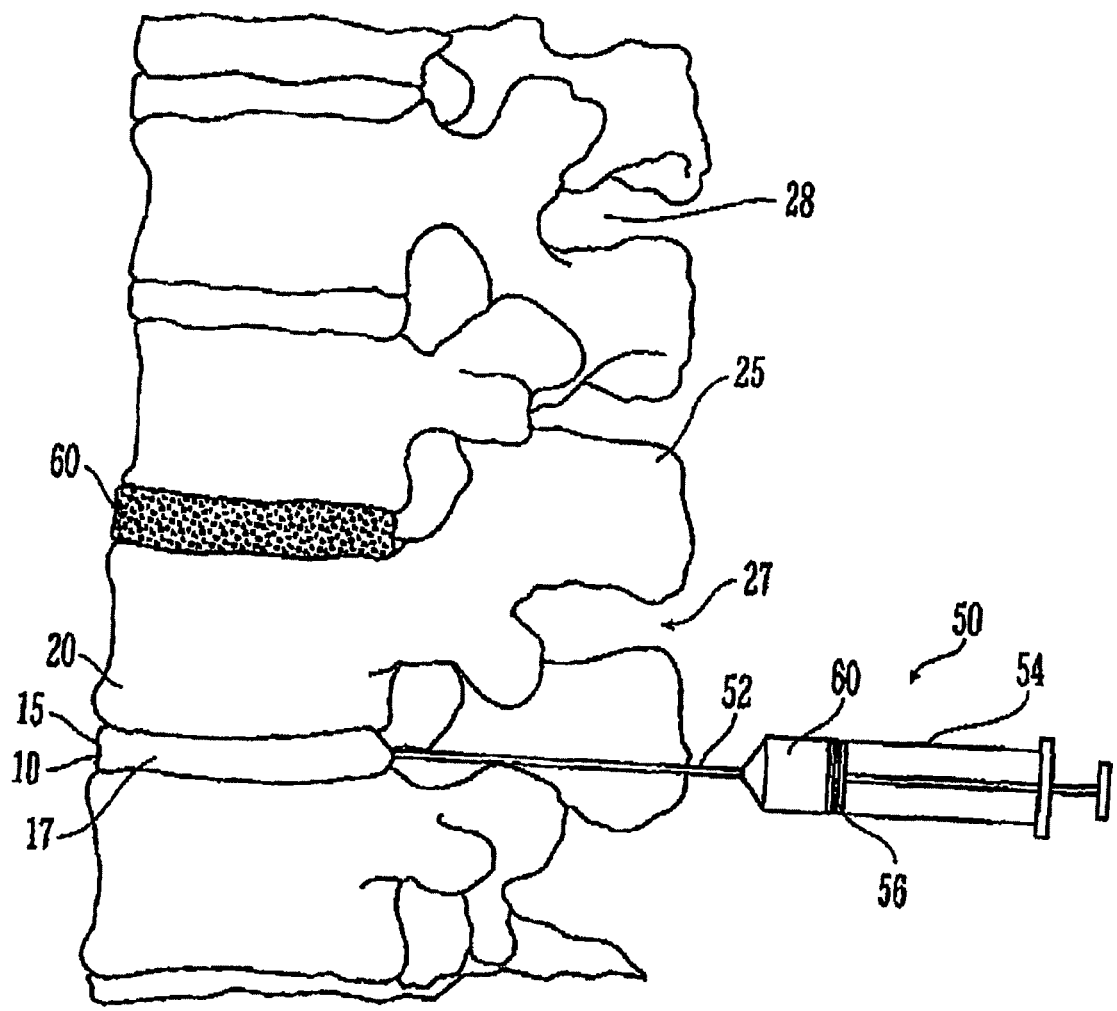
FIG. 1 illustrates the injection of a hydrogel of the present invention posteriorly into the spinal region of a patient and through the annulus of the disc using a syringe that contains the hydrogel solution and that has a needle.

The present invention relates to novel compositions and methods that permit the insertion of a flowable chemically cross-linked hydrogel at a selected site in a mammal via injection through the dermis by needle, by minimally-invasive procedure or by a surgical procedure. More particularly, it has now been found that polymer blends or copolymers of poly(vinyl alcohol) (PVA) chemically cross-linked with a second polymer are useful in production of a hydrogel that is an elastic solid at ambient (i.e., room temperature) (about 20° C. to about 27° C.) or lower where it can be stored until use, and undergoes thermal transition at it's melting point such that the chemically cross-linked hydrogel is able to flow and, therefore, is injectable into, for example, a damaged nucleus of an intervertebral disc. The hydrogel then forms a solid elastic hydrogel when cooled to a temperature below its melting point but above the physiological body temperature (about 36° C. to about 38° C.).

Compositions

In one embodiment, the present invention provides a injectable hydrogel composition comprising: water; and poly(vinyl alcohol) chemically cross-linked with a second polymer to form a cross-linked resin, wherein the second polymer is selected from the group consisting of: a polyhydric alcohol compound, a polyvalent epoxy compound, a polyvalent amine compound, a dialdehyde compound, a diisocyanate compound, and mixtures thereof, wherein the cross-linked resin has a degree of cross-linking of from about 0.0001 mol/mL to about 0.002 mol/mL, and wherein the hydrogel is flowable when heated above its melting point. Methods of making and using such hydrogels are also disclosed herein.

Hydrogels are materials whose physical state is between that of a solid and of a liquid. Gels consist of polymeric (i.e., long chain) molecules linked together to form a three-dimensional network and are embedded in a liquid medium. The liquid medium in the compositions of the present invention comprises water. Preferably, the water is deionized water.

The hydrogels according to the present invention comprise poly(vinyl alcohol) ("PVA") as a major component. Polyvinyl alcohols are commonly divided into "fully hydrolyzed" and "partly hydrolyzed" types, depending on how many mole-percent of residual acetate groups remain in the molecule. Polyvinyl alcohols can be manufactured from polyvinyl acetate by alcoholysis using a continuous process. By varying the degree of polymerization of the polyvinyl acetate and its degree of hydrolysis (saponification) a number of different grades can be supplied. Typically, suitable polyvinyl alcohols for the practice of the present invention have a degree of hydrolysis (saponification) of about 80-100 percent, preferably about 95-99.8 percent. The degree of polymerization of suitable polyvinyl alcohols for the practice of the present invention is preferably in the range of from about 100 to about 20,000 repeat units, more preferably from about 1,000 to about 10,000 repeat units, and most preferably from about 1,300 to about 5,000 repeat units. PVA having a degree of polymerization of about 3,300 repeat units is especially preferred.

PVA is selected for use in the present invention based upon its biocompatibility and stability at various hydration states. For the purposes of the present invention, a suitable PVA hydrogel will have a moisture content of at least 5% w/w of the overall hydrogel, preferably at least 10%, 15%, 20%, 25%, 30%, 35%, 40%, 50%, 60%, 70%, or 80% w/w of the overall hydrogel.

In preferred embodiments of the present invention, the hydrogels further comprise poly(vinyl pyrrolidone) ("PVP") as a secondary component. As disclosed in U.S. Pat. No. 7,214,245, which is incorporated herein by reference in its entirety, PVP may be added to enhance the long-term stability of the PVA system. Preferably, the PVP is present in the hydrogels of the present invention at a concentration of from about 0.05% (w/w) to about 0.30% (w/w) and, more preferably from about 0.14% (w/w) to about 0.22% (w/w). A mixture of PVA and PVP can be made, for example, by heating an aqueous solution of PVA and PVP at a temperature of from about 115° C. to about 130° C. for from about 5 to about 60 minutes.

The hydrogels according to the present invention further comprise a second polymer whose function is to chemically cross-link with the PVA to form a cross-linked network. As used herein, the term "chemically cross-link" refers to the formation of covalent bonds between, for example, polymer reactants. In preferred embodiments, the second polymer is selected from the group consisting of: a polyhydric alcohol compound, a polyvalent epoxy compound, a polyvalent amine compound, a dialdehyde compound, a diisocyanate compound, and mixtures thereof.

Examples of a polyhydric alcohol include, for example, (poly)propylene glycol, (poly)ethylene glycol, and (poly)glycerin.

Examples of a polyvalent epoxy compound include, for example, (poly)ethylene glycol diglycidyl ether, 1,3-butadiene diepoxide, ethylene glycol diglycidyl ether, and 1,7-octadiene diepoxide.

Examples of a polyvalent amine include, for example, (poly)ethyleneimine, tetramethylenediamine, hexamethylenediamine, octamethylenediamine, and decamethylenediamine.

Examples of a dialdehyde compound include, for example, gluteraldehyde, PEG-dialdehyde, glyoxal, formaldehyde and malonaldehyde.

Examples of a diisocyanate compound include, for example, hexamethylene-diisocyanate and ethyl ester 1-lysine diisocyanate.

Each of the aforementioned groups of second polymers includes a functional group that reacts with the hydroxyl group on PVA to form chemical cross-links.

The second polymer is preferably present in the composition at a concentration of from about 6% (w/w) to about 40% (w/w), more preferably from about 19% (w/w) to about 38% (w/w) and, most preferably from about 25% (w/w) to about 33% (w/w).

In preferred embodiments of the present invention, PVA is cross-linked with a polyvalent epoxy compound. (Poly)ethylene glycol diglycidyl ether (PEG-DGE) is the preferred cross-linking second polymer when the second polymer is a polyvalent epoxy compound and is preferably present in the composition at a concentration of from about 6% (w/w) to about 40% (w/w), more preferably from about 19% (w/w) to about 38% (w/w) and, most preferably from about 25% (w/w) to about 33% (w/w). Preferably, the PEG-DGE employed in the hydrogels of the present invention has a molecular weight of from about 526 Da to about 4600 Da. In embodiments where PEG-DGE is employed having a molecular weight of about 526 Da, the resultant hydrogel can have an elastic modulus of from about 0.03 MPa to about 1.8 MPa.

In other preferred embodiments of the present invention, PVA is cross-linked with a polyhydric alcohol. (Poly)ethylene glycol (PEG) is the preferred cross-linking second polymer when the second polymer is a polyhydric alcohol and is preferably present in the composition at a concentration of from about 6% (w/w) to about 40% (w/w), more preferably from about 8% (w/w) to about 30% (w/w) and, most preferably from about 12% (w/w) to about 18% (w/w). PEG for use in the present invention preferably has a molecular weight of from about 100 to about 10,000 g/mol, more preferably from about 526 to about 4,600 g/mol and, most preferably from about 526 to about 2,000 g/mol. Generally, as the molecular weight of the second polymer is increased, the swelling ratio (V/Vo) will increase as will the compressive modulus of the hydrogel and the viscosity of the melted hydrogel.

In preferred embodiments of the present invention, the hydrogel compositions of the present invention include an imaging agent. The inclusion of an imaging agent allows the user to image the sample as it is injected into the body, thereby assisting in the proper placement of the implanted hydrogel because the implanted material can be visualized under X-rays. Imaging agents preferably may be included in the hydrogels of the present invention in amounts up to about 25% by weight. In a preferred embodiment, the hydrogels of the present invention comprises from about 2 weight % to about 25 weight % of an imaging agent; more preferably from about 7 weight % to about 15 weight %. In a particularly preferred embodiment, the hydrogels of the present invention comprise about 11 weight % of an imaging agent. Typical imaging agents suitable for use in the present invention include barium sulfate, iodine, or any heavy metal powder that provides the necessary radio-opacity under external imaging. The imaging agent is added to the hydrogels of the present invention while the composition exists in a liquid phase and is mixed therein to preferably obtain uniform distribution in the solution. Barium sulfate is the preferred imaging agent.

In preferred embodiments of the present invention, the cross-linked resin has a degree of cross-linking of from about 0.0001 mol/mL to about 0.002 mol/mL, more preferably from about 0.0007 mol/mL to about 0.0011 mol/mL, and most preferably about 0.0009 mol/mL+/−0.0002 mol/mL. This amount or degree of cross-linking is sufficient to impart mechanical and visco-elastic properties to the system without imparting rigidity to the hydrogels. Accordingly, a hydrogel of the present invention is elastic at ambient temperature and is flowable when heated to above its melting point. As used herein, the term "flowable" means that the composition transforms from a solid to a liquid and, therefore, is able to flow, i.e., to move with a continual change of place among the constituent polymer chains. The viscosity of the hydrogel compositions of the present invention for injection at a temperatures of 95° C. is from about 11 Pa*s to about 77 Pa*s. Accordingly, when heated to above their melting temperatures, hydrogel compositions of the present invention are injectable directly into, for example, a cavity formed by a damaged nucleus of a patient's intervertebral disc or into a shaped mold. The hydrogel then forms a solid elastic hydrogel when cooled to a temperature below its melting point but above the physiological body temperature (about 36° C. to about 38° C.) due to the PVA interchain and intrachain hydrogen bonding. These hydrogen bonds, known as interpolymer complexes, serve as secondary, physical crosslinks, providing networks with additional stability and mechanical properties.

The limited degree of chemical cross-linking of the hydrogels of the present invention also restricts swelling of the hydrogels. For example, the hydrogel compositions according to the present invention preferably exhibit a swelling volume change of about 11% to about 17% in a 0.16 MPa osmotic solution. Compared to prior art hydrogels, less polymer component is required in the compositions of the present invention to achieve the same mechanical properties. Less polymer in a hydrogel system typically translates into less volume of water required and, hence, less swelling.

Process for Making Hydrogels

In another embodiment, the present invention provides a process for making a hydrogel composition as described above. The process comprises the steps of: forming an aqueous solution of poly(vinyl alcohol) and water in a sealed pressurized container; heating the aqueous solution to a temperature of from about 90° C. to about 125° C.; cooling the aqueous solution to a temperature of from about 70° C. to about 80° C.; adding the second polymer and a catalyst to the aqueous solution, wherein the catalyst is selected from the group consisting of: an acid and a base; cooling the solution to ambient temperature; chemically cross-linking the PVA and the second polymer; and holding the solution at ambient temperature for a period of from about 1 to about 48 hours to allow for the completion of chemical cross-linking and formation of a hydrogel composition that is flowable when heated above its melting point. This process is detailed in the working examples below.

In preferred embodiments of the present invention, a catalyst is employed to increase the rate of the cross-linking reaction. The catalyst can be either an acid or a base, depending on the chemistry of the composition. Whether an acid or a base is employed can readily determined by the skilled artisan. For example, in embodiments where the second polymer is a dialdehyde polymer, then the cross-linking reaction is preferably catalyzed with an acid. In embodiments where the second polymer is (poly)ethylene glycol diglycidyl ether, then the cross-linking reaction is preferably catalyzed with a base. Suitable acid catalysts include HCl, and $H_2SO_4$. Suitable base catalysts include NaOH, and $Ba(OH)_2$.

Chemical cross-linking can occur by either exposing the aqueous composition comprising PVA, the second polymer, optionally PVP, and any other additive to heat or ionizing radiation. In embodiments where heat is employed to chemically cross-link the compositions, preferably an aqueous solution of PVA, the second polymer, and any optional component(s) is heated to a temperature of from about 60° C. to about 85° C. for from about 20 minutes to about 60 minutes in, for example, an autoclave, followed by storing the composition at room temperature for from about 1 to about 48 hours to allow for completion of chemical cross-linking. In other embodiments of the present invention, multiple heating steps may be employed.

In embodiments where radiation is employed to cross-link the compositions, the ionizing radiation can be electron beam radiation, ultraviolet (UV) radiation, or gamma radiation. In preferred embodiments, the ionizing radiation is gamma radiation or electron beam. In preferred embodiments, the total radiation dose is suitably from 1-1,000 kGy, preferably 50-1,000 kGy, more preferably 10-200 kGy. The radiation dose rate is suitably about 0.1-25 kGy/min, preferably about 1-10 kGy/min. In preferred embodiments, the irradiation dose used is within 20% of the optimum irradiation dose, preferably within 10%, more preferably within 7% of the optimum irradiation dose. The optimum irradiation dose is typically specific to each polymer.

Applications

As discussed above, when heated to above their melting temperatures, hydrogel compositions of the present invention are injectable directly into, for example, a cavity formed by a damaged nucleus of a patient's intervertebral disc or into a shaped mold. In embodiments where the hydrogel is injected into a mold, the mold is desirably configured to a shape generally conforming to that of the natural disc nucleus pulposis.

In one embodiment, hydrogels of the present invention, once solidified, exhibit adequate mechanical properties as well as biocompatibility to serve as a useful prosthetic nucleus for replacement or augmentation of nucleus pulposus in spinal discs in mammals, including humans. Accordingly, the present invention is further directed towards methods of implanting a hydrogel into a selected site of a mammal which may comprise injecting the flowable (heated) hydrogel composition into a cavity of an intervertebral disc of a patient who has had at least a portion of nucleus pulposus tissue removed from the intervertebral disc. The thermogelling hydrogel is injected into the selected site in a mammal as a liquid at an elevated temperature and solidifies to form a solid implant as the hydrogel cools to physiological body temperature at the selected site in the mammal.

In a particular embodiment, the thermogelling hydrogel can be injected into a cavity formed by the annulus of a spinal disc as a liquid to form a solid implant in situ that is retained by the annulus of the disc. One of skill in the art can inject the hydrogels of the present invention in their heated viscous liquid state into the nuclear cavity of an intervertebral disc using a standard microdiscetomy approach. In one embodiment, the hydrogel can be injected percutaneously through the skin directly into the cavity formed by the annulus of the disc.

More preferably, as shown in FIG. 1, the heated liquid hydrogel 60 can be inserted from the posterior side 27 of the spinal column 28 past the spinous process 25 into the cavity 17 formed by the annulus 15 of the disc 10, using a syringe 50 that contains the hydrogel composition 60. Typically, the syringe 50 contains a needle 52, and uses to plunger 56 that can be adjusted to expel the hydrogel composition 60 from the syringe housing 54. FIG. 1 also demonstrates the visualization of the solid hydrogel with an imaging agent 62 in the disc 10 following injection of the hydrogel composition 60 and subsequent solidification as the hydrogel composition 60 cools to physiological body temperature.

In an alternate embodiment, the hydrogel can be injected through one or more cannulas (or other device) that have been inserted into the patient down to the disc site in order to create access to the annulus. In this regard, the cannula provides a passageway from outside the patients body down to the disc, preferably in a manner where the user can visualize where the needle will be inserted into the disc or the incision in the disc annulus will be made. In yet another embodiment, the hydrogel can be injected into a selected site of a mammal by a minimally-invasive surgical procedure. The hydrogels in one embodiment may be injected by using devices having a needle that ranges from about 6 gauge to about 28 gauge, with preferred devices containing an about a 14 to about 22 gauge needle. The present invention could be used for complete replacement of the nucleus puloposus or simply as an augmentation following injury or partial discectomy. Implantation of the prosthetic nucleus is expected to provide relief from pain as well as provide for functional disc activity.

For the nucleus pulposus replacement or augmentation to be successful, in addition to biocompatibility of the material in general and the appropriate local tissue response at the site of implantation, there are several mechanical requirements which preferably will be achieved. The nucleus replacement biomaterial should provide adequate tension to the annulus fibrosus upon loading in order to tension the annulus fibers and thereby restore biomechanical behavior of the disc to that of the normal intervertebral disc. The biomechanics of the restored disc should behave similar to the intact disc in compression, flexion and torsion. In addition, the device should restore the time dependent biomechanical behavior so that the implanted disc behaves similar to the intact normal disc in creep and stress relaxation. Fatigue of the implant in the disc should be able to withstand the life of the patient without degradation to the point of necessitating a revision surgery. Preferably there should be no appreciable wear debris from the device in the disc space necessitating a revision surgery due to pain or inflammation. It may or may not be desirable to appear radiopaque upon X-ray. Also, the nucleus replacement or augmentation would ideally be able to be implanted in a minimally invasive manner or injected percutaneously.

Thus, in one embodiment, the present invention provides a process for forming an intervertebral implant directly in a patient, the process comprising the steps of: heating a hydrogel composition to above its melting point such that the composition is flowable, the hydrogel composition comprising: water; and poly(vinyl alcohol) chemically cross-linked with a second polymer to form a cross-linked resin, wherein the second polymer is selected from the group consisting of: a polyhydric alcohol compound, a polyvalent epoxy compound, a polyvalent amine compound, a dialdehyde compound, a diisocyanate compound, and mixtures thereof, wherein the cross-linked resin has a degree of cross-linking of from about 0.0001 mol/mL to about 0.002 mol/mL, and wherein the hydrogel is flowable when heated above its melting point; and injecting the flowable hydrogel composition into a cavity of an intervertebral disc of a patient who has had at least a portion of nucleus pulposus tissue removed from the intervertebral disc.

In yet another embodiment, the present invention provides a process for forming an intervertebral implant, the process comprising the steps of: heating a hydrogel composition to above its melting point such that the composition is flowable, the hydrogel composition comprising: water; and poly(vinyl alcohol) chemically cross-linked with a second polymer to form a cross-linked resin, wherein the second polymer is selected from the group consisting of: a polyhydric alcohol compound, a polyvalent epoxy compound, a polyvalent amine compound, a dialdehyde compound, a diisocyanate compound, and mixtures thereof, wherein the cross-linked resin has a degree of cross-linking of from about 0.0001 mol/mL to about 0.002 mol/mL, and wherein the hydrogel is flowable when heated above its melting point; injecting the flowable hydrogel composition into a mold; and cooling the hydrogel composition.

To accomplish the goals of the device, the hydrogel biomaterial itself should display certain material properties. The material should have a modulus of elasticity and Poisson's ratio such that a complete filling of a nucleus cavity or an augmentation to a nucleus cavity to a given pressure or disc height will succeed in restoration of the biomechanical behavior of a normal disc. One way that the implant material can provide an interfacial stress on the annulus fibrosus inner surface is through the Poisson effect. The material can, upon loading, deform radially. With an elastomeric material, such as the hydrogel family, a relatively high Poisson ratio, in the range of about 0.35 to about 0.4999 can be achieved. The higher the Poisson ratio, the higher the interfacial stress can be transmitted to the tumulus and potentially more complete restoration of biomechanics can be achieved.

Additional mechanical behavior of the hydrogel material of the present invention is important. The hydrogel should be able to withstand from about 10 million to about 40 million cycles of compression-compression fatigue to physiological loading levels for the nucleus. Shear fatigue will also be an important material property because of the off-axis loading that may take place during the life of the device. Time-dependent behavior of the hydrogel material should be such that the material can creep over a constant activity load (for example, standing or walking during the day) but be able to fully or nearly fully recover from the deformation during the resting state of the device (for example, while the patient is lying prone in a resting state where the load levels are much lower than the active state). The natural disc undergoes creep and recovery in a diurnal cycle and if the implant material also undergoes a similar mechanical behavior, it is important that it be in a similar time frame. The wear properties of the material are also important, and the wear debris produced from the device, if any, should be in a form that does not cause an unacceptable inflammatory response that would lead to permanent and irreparable damage to the surrounding tissues at or near the implantation site.

The modulus of elasticity also has an effect on the ability of nucleus replacement implants to perform successfully. Compressive biomechanics similar to a fully functional disc are achieved with a modulus of elasticity from about 10 KPa to about 10,000 KPa and normal mechanical behavior is restored with a modulus of elasticity from about 10 KPa to about 5,000 KPa. More preferably an implant modulus of about 50 KPa to about 1,500 KPa is in a range to restore the compressive stiffness. It is contemplated that a threshold exists where the modulus of the implant affects tensioning the annulus fibers, after which the lateral deformities associated with the higher modulus do nothing to further the stiffness of the system.

Insufficient filling of the nucleus cavity contribute significantly to the stiffness of the disc and its performance in the spinal column. More specifically, the effect of height and diameter variation has a significant effect on the stiffness of the disc. In cases where a denucleated disc is not restored to its intact normal diameter and height, the lack of proper interaction between the hydrogel implant and the annulus resulted in limited restoration of the functional spinal column unit. The functional spinal column unit referring to a disc and two adjoining vertebrae. However, in cases where the denucleated disc is fully expanded or restored to its normal intact height and/or diameter almost complete restoration of the stiffness is observed. Testing has further shown that expanding a denucleated disc to more than its normal intact height, or expanding the denucleated disc to more than its normal intact diameter (width) provides almost complete restoration of the stiffness of the disc.

With the injectable hydrogels according to the present invention, restoring the "fit and fill" of the disc easily be achieved by the amount of hydrogel material that is injected. By varying the amount of hydrogel material injected into the disc cavity, the fit and fill of the disc can be tailored for each disc and each patient during the procedure, which is advantageous over preformed implants. In addition, discs can be "overfilled" with the injectable hydrogels of the present invention without compromising the performance of the disc. The amount of hydrogel material that may be injected into a typical patient disc should preferably be proportional to the volume of the cavity that the implant is intended to fill. Such a cavity may be created, for example, from a nucleotomy. In one embodiment, the ratio of the volume of the hydrogel material to be injected into the cavity ("implant volume") to the volume of the cavity ("cavity volume") is preferably about 0.8 to about 1.5. In a preferred embodiment, the implant volume-to-cavity volume ratio should be about 1.0 to about 1.13. These volume ratios are illustrative only and may vary by the size of the patient and the specific disc that needs to be restored. For the purposes of determining such ratios, the volume of the cavity can be approximated, for example, from the radius of the cavity (r) and the disc height (h) using the following equation $V=\pi r^2 h$. See Joshi et al., *Society for Biomaterials*, Annual Meeting 2003, Reno.

Although the present invention has been principally described in connection with injecting the hydrogel compositions of the present invention into the nuclear cavity of an intervertebral disc, one of ordinary skill in the art would understand that a variety of other applications exist for such biomaterials such as, for example, wound care, disc replacement or augmentation, cartilage replacement, joint replacement, surgical barriers, gastrointestinal devices, cosmetic and reconstructive surgery, and breast enlargement.

The following examples are provided for the purpose of further illustrating the present invention but are by no means intended to limit the same.

EXAMPLES

Example 1

Preparation of and Mechanical Testing of PVA/PVP/PEG-DGE Hydrogel Compositions Mechanical testing was performed to demonstrate the properties of the resultant PVA/PVP/PEG-DGE hydrogels. PVA/PVP/PEG-DGE hydrogel compositions were made by preparing an aqueous PVA/PVP solution (14.32% w/w) by mixing PVA ((Mowiol 28-99: 145 kDa; 99-99.8 mol % hydrolyzed) supplied by Sigma Aldrich), PVP (C-30; MW=58,000 Da), Barium Sulfate (1-10 μm) and deionized water in a sealed glass bottle and heating to 121° C. for 30 minutes in an autoclave. The ratio of PVA to PVP was 99:1. A 4% to 15% concentration of barium sulfate in the resultant hydrogel composition was sufficient to make the hydrogels radiopaque. The addition of barium sulfate was an optional step. Solutions were then stored at 75° C. in a water bath, the solution was maintained at 75° C.±5° C. during the addition of PEG-DGE (MW=526 Da, supplied by Sigma Aldrich) and 100 μL of 10M NaOH. NaOH was added to create a basic condition for the ring opening reaction of the PEG-DGE to enable it to crosslink to PVA. The solution was left at room temperature for 1-48 hours to allow chemical crosslinking. The initial concentration ranges of the components of the precursor polymer composition are summarized in Table 1. The resultant polymer solutions water content is shown in Table 2.

Also shown in Table 1 is the cross-link density of the hydrogel as was determined by the following method. The PVA/PVP/PEG-DGE hydrogel composition was molded into a 2 mm thick films. 14 mm discs were cut from this film and dried for 5 days. The dried discs were weighed in air and heptane to determine dry polymer volume. Each disc was swollen in 35 mL of PBS at 37° C. for 7 days. After swelling the volume was measured and the polymer volume fraction ($v_{2,s}$) was found by comparing the dry polymer volume to the swollen polymer volume. Tensile samples, 5 mm wide and 30 mm long were cut from the 2 mm thick PVA/PVP/PEG-DGE hydrogel films. Samples were then swollen in PBS at 37° C. for 7 days. Each strip was then stretched up to 15% strain at a rate of 10% strain per minute while submerged in 37° C. PBS. Normalized tensile modulus, G, was calculated from the tensile test and is described by the following equation:

$$G = \frac{\tau}{\alpha - 1/\alpha^2} v_{2,s}^{1/3}.$$

Molecular weight between crosslinks $\overline{M}_c$ is determined using a model by Peppas, N. A. and E. Merrill, *Crosslinked Poly(vinyl alcohol) Hydrogels as Swollen Elastic Networks*, Journal of Applied Polymer Science, Vol. 21, p. 1763-1770 (1977), which is incorporated herein by reference in its entirety:

$$\frac{\tau}{(\alpha - 1/\alpha^2)} = RT\rho_{2,r}\left(\frac{1}{\overline{M}_c} - \frac{2}{\overline{M}_n}\right)\left(\frac{v_{2,s}}{v_{2,r}}\right)^{1/3}$$

where $\tau$ is the tensile stress, $\rho_{2,r}$ is the density of the gel in the relaxed state, $\alpha$ is the normalized elongation of the sample, $v_{2,r}$ is the polymer volume fraction of the gel in the relaxed state, R is the ideal gas constant and $\overline{M}_n$ is the average molecular weight of the polymer. Crosslink density, $\rho_x$, is calculated using the equation:

$$\rho_x = \frac{1}{\overline{v}\overline{M}_c}$$

where $\overline{v}$ is the specific volume of the polymer. See Martens, P. and K. S. Anseth, *Characterization of Hydrogels Formed from Acrylate Modified Poly(vinyl alcohol) Macromers*. Polymer, 41, pp. 7715-7722 (2000), which is incorporated herein by reference in its entirety.

TABLE 1

Concentrations of the Components of the Precursor Polymer Solutions

| Material | Sample Composition (% w/w) | |
|---|---|---|
| | A | B |
| Polyvinyl alcohol 145 kDa | 18.70 | 16.10 |
| Polyethylene glycol digylcidyl ether (PEG-DGE) 526 Da | 19.84 | 30.96 |
| Polyvinyl pyrrolidone 58 kDa | 0.19 | 0.16 |
| Deionized water | 55.70 | 47.96 |
| Barium Sulfate | 5.57 | 4.79 |
| Molecular weight between crosslinks (g/mol) | 6639 ± 1040 | 1321 ± 238 |
| Crosslink density (mol/mL) | 0.0002 ± 0.0000 | 0.0009 ± 0.0002 |

TABLE 2

Concentrations of Water of the Resultant Polymer Solutions

| Resultant Material | Sample Composition | | |
|---|---|---|---|
| | A minus PEG-DGE | A | B |
| Water Content (% w/w) | 68.44 ± 0.27 | 53.92 ± 0.69 | 46.06 ± 0.55 |

Figure 2:
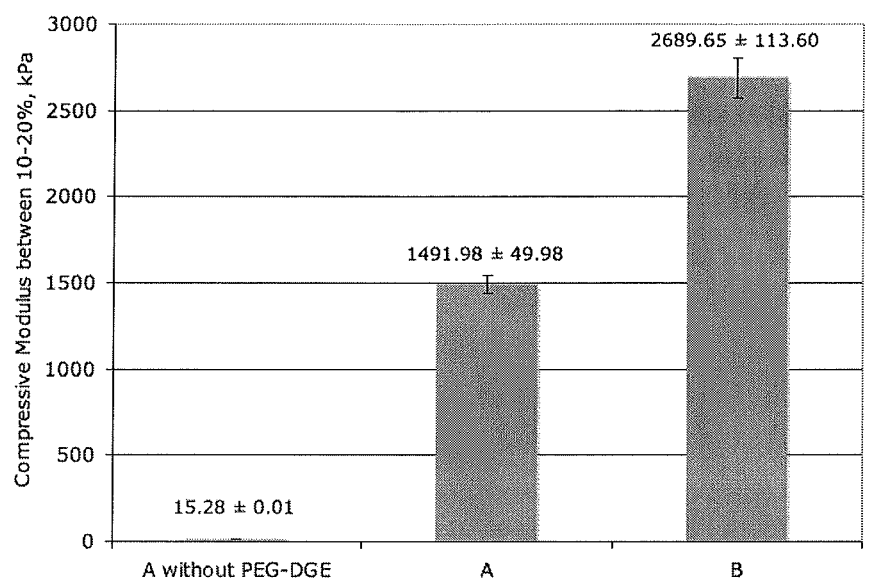
FIG. 2 illustrates the compressive modulus of two formulations of the PVA/PVP/PEG-DGE hydrogel and shows the difference between the modulus of one formulation without PEG-DGE.

Cylindrical samples (n=3) (approximately 5 mm in height and 9.5 mm in diameter) were molded directly from the PVA/PVP/PEG-DGE resultant hydrogel composition at 90° C. by injecting the flowable PVA/PVP/PEG-DGE resultant hydrogel composition into polyvinyl chloride tubing followed by sealing the ends with caps. Hydrogels were allowed to form at room temperature for 48 hours. The test cylinders were cut and removed from the tubing and tested in compression (at a rate of 100% strain/min) on an Instron Universal Testing Machine (Model #4442), a chord modulus was taken between 10 and 20% strain. FIG. 2 demonstrates that there is a significant increase in compression modulus for cylinders made from the PVA/PVP/PEG hydrogel compositions according to the present invention when compared with control cylinders molded from the same grade of PVA alone (i.e., no PEG-DGE).

Example 2

Polymer Content of the PVA/PVP/PEG-DGE Hydrogel Composition

Three PVA/PVP/PEG-DGE hydrogel compositions were formed as described in Example 1. The water content was calculated for the three PVA/PVP/PEG-DGE hydrogel compositions to be 53.56% on average with a standard deviation of 0.64 (See Table 3); the remaining 46.44% is polymer and barium sulfate.

TABLE 3

Concentration of Components of the Resultant PVA/PVP/PEG-DGE Hydrogel Composition

| Material | Composition (% w/w) |
|---|---|
| Water | 46.44 ± 0.64 |
| Polymer (PEG/PVP/PEG-DGE) and Barium Sulfate | 53.56 ± 0.64 |

Example 3

Unconstrained Osmotic Swelling

Figure 3:
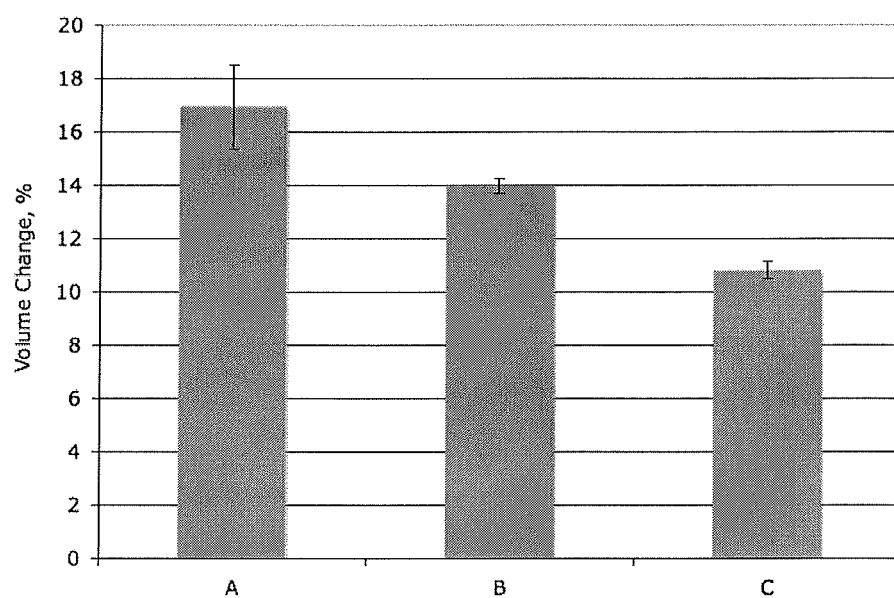
FIG. 3 illustrates the percent volume change of three formulations of the PVA/PVP/PEG-DGE hydrogel when swollen in a PEG solution with the osmotic pressure of 0.16 MPa.

The osmotic pressure of the intervertebral disc ranges from approximately 0.05 to 0.3 MPa, ideally the hydrogel composition would maintain its volume over this range of osmotic environments. The hydrogel compositions from Example 2 (initial concentrations of components show in Table 3) were placed in PEG solution with an osmotic pressure of 0.16 MPa. PEG solutions are known to have predictable osmotic pressures, so solutions with specific concentrations of PEG can be made resulting in a range of osmotic pressures. The change in volume in an unconstrained environment (i.e., where nothing is touching or constraining the hydrogel, thus, it is free to swell) can then be determined to determine how the hydrogel composition would respond in different osmotic environments. The volume of PEG solution was sufficient to allow "sink" conditions (i.e., the volume of PEG liquid is in such excess that the osmotic pressure won't change when water comes out of the gel), where the ratio of volume of solution to mass of hydrogel composition was approximately 70:1. The solutions were maintained at 37° C. for 7 days. FIG. 3 shows the change in volume for three hydrogel compositions, the initial concentration ranges of the components of the precursor polymer composition are summarized in Table 4. The resultant polymer solutions water content is shown in Table 5.

TABLE 4

Concentrations of the Components of the Precursor Polymer Solutions

| Material | Sample Composition (% w/w) | | |
|---|---|---|---|
| | A | B | C |
| Polyvinyl alcohol 145 kDa | 18.70 | 17.29 | 16.10 |
| Polyethylene glycol digylcidyl ether (PEG-DGE) 526 Da | 19.84 | 25.84 | 30.96 |
| Polyvinyl pyrrolidone 58 kDa | 0.19 | 0.17 | 0.16 |
| Deionized water | 55.70 | 51.52 | 47.96 |
| Barium Sulfate | 5.57 | 5.15 | 4.79 |

TABLE 5

Concentrations of Water of the Resultant Polymer Solutions

| Resultant Material | Sample Composition | | |
|---|---|---|---|
| | A | B | C |
| Water Content (% w/w) | 53.92 ± 0.69 | 52.83 ± 0.37 | 46.06 ± 0.55 |

Example 4

Mechanical, Osmotic Swelling and Viscosity Analysis for Compositions of Varying NaOH Addition PVA/PVP/PEG-DGE hydrogel compositions were prepared generally as described in Example 1, except for varying the NaOH addition from 0 to 600 µL. A minimum modulus of 50 kPa is needed to restore healthy tension in the annulus fibers of the intervertebral disc, which is achieved with the PVA/PVP/PEG-DGE hydrogel composition with 0 µL of NaOH. Mechanical testing was performed as described in Example 1. The PVA/PVP/PEG-DGE hydrogel compositions are for an injectable application, with increasing NaOH addition the hydrogel viscosity increases until it is no longer injectable at 600 µL. Viscosity testing was performed per ASTM F451-08 (ASTM F451-08, Standard Specification for Acrylic Bone Cement). The PVA/PVP/PEG-DGE hydrogel compositions were heated to 95° C. and injected with an Instron (Model 1331) in displacement control. A steady-state load was achieved while the PVA/PVP/PEG-DGE hydrogel compositions were being injected and from this steady-state load the viscosity of the hydrogel is calculated. Unconfined swelling of the PVA/PVP/PEG-DGE hydrogel compositions was determined using the method described in Example 3. The swelling value is represented as the swollen volume (V) divided by the original volume ($V_o$), this value is the swelling ratio of the hydrogel. Compressive modulus, swelling ratio and viscosity of the PVA/PVP/PEG-DGE hydrogel compositions with varying NaOH addition is shown in Table 6.

TABLE 6

Compressive Modulus, Swelling and Viscosity for PVA/PVP/PEG-DGE Hydrogel Compositions with Varying Amounts of NaOH

| NaOH [µL] | 48 Hour Modulus [MPa] | Swelling $V/V_0$ | Viscosity [Pa * s] |
|---|---|---|---|
| 0 | 0.64 ± 0.02 | 0.970 ± 0.003 | 13.92 ± 2.13 |
| 40 | 1.05 ± 0.03 | 1.033 ± 0.015 | not taken |
| 60 | 1.02 ± 0.15 | 1.062 ± 0.011 | not taken |
| 80 | 1.25 ± 0.04 | 1.020 ± 0.007 | not taken |
| 100 | 1.34 ± 0.08 | 1.121 ± 0.006 | 26.77 ± 4.12 |
| 200 | 1.83 ± 0.07 | 1.100 ± 0.005 | 32.67 ± 4.63 |
| 400 | | | |
| 600 | | | |

Example 5

Mechanical and Viscosity Analysis for Compositions of Varying PEG-DGE Concentrations Resultant PVA/PVP/PEG-DGE hydrogel compositions were prepared generally as described in Example 1, except for varying the PEG-DGE concentration from 3.62 to 40.03% w/w. It is well known that a minimum modulus of 50 kPa is needed to restore healthy tension in the annulus fibers of the intervertebral disc (see, e.g., Joshi, A. B., *Mechanical Behavior of the Human Lumbar Intervertebral Disc with Polymeric Hydrogel Nucleus Implant: An Experimental and Finite Element Study*. 2004, Drexel University), which is achieved with the PVA/PVP/PEG-DGE hydrogel composition with 8.89% w/w of PEG-DGE. Mechanical testing was performed as described in Example 1. The PVA/PVP/PEG-DGE hydrogel compositions are for an injectable application, with increasing PEG-DGE concentration the hydrogel viscosity increases until it is no longer injectable at 40.03% w/w. Viscosity testing was performed as described in Example 4. Compressive modulus and viscosity of the PVA/PVP/PEG-DGE hydrogel compositions with varying PEG-DGE amounts is shown in Table 7.

TABLE 7

Compressive Modulus, Swelling and Viscosity for PVA/PVP/PEG-DGE Hydrogel Compositions with Varying Amounts of PGE-DGE

| Polyvinyl alcohol 145 kDa [% w/w] | Sample Compositions | Polyethylene glycol diglycidyl ether 526 Da [% w/w] | 48 Hour Modulus [MPa] | Viscosity |
|---|---|---|---|---|
| 22.48 | A | 3.62  | 0.032 ± 0.002 | not taken |
| 21.85 | B | 6.33  | 0.036 ± 0.001 | not taken |
| 21.25 | C | 8.89  | 0.049 ± 0.003 | 11.75 ± 3.04 |
| 18.70 | D | 19.84 | 1.34 ± 0.08   | 26.77 ± 4.12 |
| 14.51 | E | 37.79 | 1.94 ± 0.17   | 77.09 ± 5.75 |
| 13.99 | F | 40.03 | not taken     | FAILED |

Example 6

Preparation of PVA/PVP/PEG/PEG-DGE Hydrogel Compositions

PVA/PVP/PEG-DGE hydrogel compositions were prepared generally as described in Example 1, except for PEG (MW=10 kDa, supplied by Sigma Aldrich) was added in addition to the PEG-DGE. Specifically the PVA/PVP/PEG/PEG-DGE hydrogel compositions were prepared by first preparing an aqueous PVA/PVP solution by mixing PVA ((Mowiol 28-99: 145 kDa; 99-99.8 mol % hydrolyzed) supplied by Sigma Aldrich), PVP (C-30; MW=58,000 Da), and deionized water in a sealed glass bottle and heating to 121° C. for 30 minutes in an autoclave. The ratio of PVA to PVP was 99:1.

Barium sulfate (1-10 um) was then dispersed into the solution by mixing in order to form a suspension. A 4% to 15% concentration of barium sulfate in the resultant hydrogel composition was sufficient to make the hydrogel radiopaque. The addition of Barium Sulfate is an optional step. A second heating followed the addition of barium sulfate at 121° C. for 30 minutes. In the second step, PEG (MW=10,000 Da supplied by Sigma Aldrich), PEG-DGE (MW=526 Da supplied by Sigma Aldrich), and 325 μL of NaOH are mixed into the PVA/PVP solution while maintaining the solution at a temperature between about 65° C. and about 100° C., preferably about 75° C. The presence of PEG served a dual role as a plasticizer of the hydrogel for injectability, as well as concentrator for increasing the polymer content of the hydrogel. NaOH was added to create a basic condition for the ring opening reaction of the PEG-DGE to enable it to crosslink to PVA. The addition of PEG resulted, upon cooling, in a phase separation, which resulted in the formation of a supernatant phase, which drew water from the hydrogel. The supernatant was removed and the resultant hydrogel was then heated to 121° C. for 30 minutes in an autoclave followed by being molded as described in Example 1.

Example 7

Addition of Buffers to Control pH of PVA/PVP/PEG/PEG-DGE Hydrogel

PVA/PVP/PEG/PEG-DGE hydrogel compositions were prepared generally as described in Example 6 for PVA/PVP/PEG/PEG-DGE hydrogels. Briefly, preparation of the hydrogel composition involved the formation of a PVA/PVP solution in a 3,3-dimethylglutaric acid buffer (pH ranging from 7.0 to 8.5) and a subsequent step where PEG and PEG-DGE was added to the PVA/PVP solution in order to dehydrate and crosslink the hydrogel and then form the resultant hydrogel and supernatant phases. The resultant dehydrated and crosslinked hydrogel phase was separated from the supernatant. After the hydrogel component is separated, it was then molded. The PEG-DGE chemical crosslinking reaction is a ring opening that occurs under basic conditions.

More specifically, in a first step, an aqueous solution of PVA (28-99; 99% hydrolyzed; Mw=145,000 Da) and PVP (C-30; Mw=58,000 Da) was prepared in 3,3-dimethylglutaric acid buffer (pH ranging from 7.0 to 8.5) at an initial polymer concentration of 20%. The solution was prepared at a temperature of between about 100° C. and about 130° C., preferably 121° C. The ratio of PVA to PVP was 99:1. In this example, Barium Sulfate (1-10 um) was then dispersed into the solution by mixing in order to form a suspension. In a second step, a precursor polymer solution was prepared by mixing PEG (MW=10,000 Da) and PEG-DGE (MW=526 Da) into the PVA/PVP solution while maintaining the solution at a temperature between about 65° C. and about 100° C., preferably about 75° C. The presence of PEG-DGE served as a chemical crosslinker for the hydrogel network. The presence of PEG served a dual role as a plasticizer of the hydrogel for injectability, as well as concentrator for increasing the polymer content of the hydrogel. The addition of PEG resulted, upon cooling, in a phase separation which resulted in the formation of a supernatant phase which drew water from the hydrogel. The supernatant, was removed and the resultant hydrogel was then molded as described in Example 1. The initial concentration ranges of the components of the precursor polymer composition are summarized in Table 8. The resultant polymer solutions water content is shown in Table 9. Osmotic swelling was performed as described in Example 2, the results of varying pH with the use of a 3,3-dimethylglutaric acid buffer is show in Table 10.

TABLE 8

Concentrations of the Components of the Precursor Polymer Solution

| Material | Sample Composition (% w/w) PVA/PVP/PEG/PEG-DGE |
|---|---|
| Polyvinyl alcohol 145 kDa | 19.54 |
| Polyethylene glycol 10 kDa | 17.28 |

TABLE 8-continued

Concentrations of the Components of
the Precursor Polymer Solution

| Material | Sample Composition (% w/w) PVA/PVP/PEG/PEG-DGE |
|---|---|
| Polyethylene glycol digylcidyl ether 526 Da | 2.60 |
| Polyvinyl pyrrolidone 58 kDa | 0.19 |
| 3,3-Dimethylglutaric acid buffer | 53.57 |
| Barium sulfate | 6.82 |

TABLE 9

Concentrations of Water of the Resultant Polymer Solutions

| | 3,3-Dimethylglutaric Acid Buffer pH | | | |
|---|---|---|---|---|
| Resultant Material | 7.0 | 8.0 | 8.5 | 9.2 |
| Water Content (% w/w) | 45.8 ± 0.4 | 48.4 ± 0.3 | 50.2 ± 0.9 | 40.4 ± 0.1 |

TABLE 10

Effect of using 3,3-Dimethylglutaric
Acid Buffer on Osmotic Swelling for
PVA/PVP/PEG/PEG-DGE Hydrogel

| 3,3-Dimethylglutaric Acid Buffer pH | Swelling $V/V_0$ |
|---|---|
| 7.0 | 1.79 ± 0.01 |
| 8.0 | 1.63 ± 0.01 |
| 8.5 | 1.66 ± 0.02 |
| 9.2 | 1.69 ± 0.01 |

Example 8

Varying MW of PEG-DGE in the
PVA/PVP/PEG-DGE Hydrogel

Figure 4:
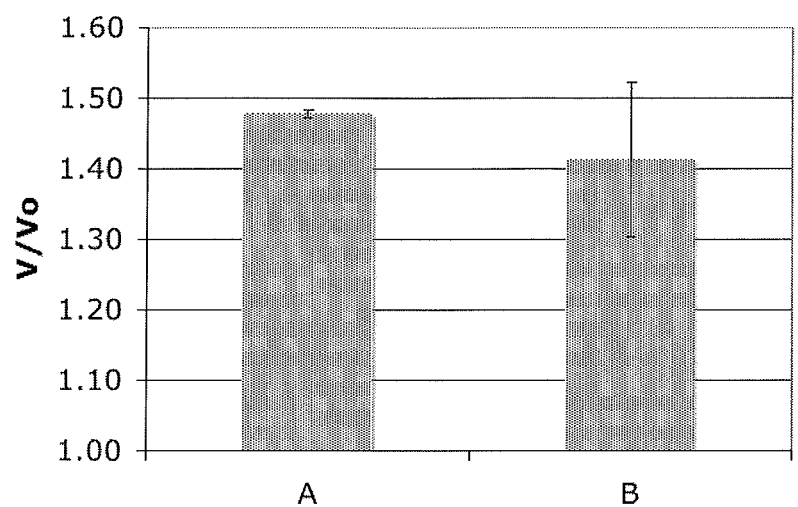
FIG. 4 illustrates the effect of PEG-DGE molecular weight (526 vs. 4600) on swelling in a PEG solution with the osmotic pressure of 0.16 MPa.

PVA/PVP/PEG/PEG-DGE hydrogel compositions were prepared generally as described in Example 6 for PVA/PVP/PEG/PEG-DGE hydrogels except the molecular weight of PEG-DGE was varied. Either PEG-DGE 526 Da (MW=526 Da supplied by Sigma Aldrich) or PEG-DGE 4600 Da (MW=4600 Da supplied by Advanced Polymer Materials Inc.). The initial concentration ranges of the components of the precursor polymer composition are summarized in Table 11. Swelling test specimens were molded and tested as described in Example 3, swelling ratios of these PVA/PVP/PEG-DGE hydrogels with differing PEG-DGE are shown in FIG. 4. The resultant polymer solutions water content is shown in Table 12.

TABLE 11

Concentration of Components of the
PVA/PVP/PEG-DGE Hydrogel Composition

| | Sample Composition (% w/w) | |
|---|---|---|
| Material | A (PEG-DGE MW = 526 Da) | B (PEG-DGE MW = 4600 Da) |
| Polyvinyl alcohol 145 kDa | 14.49 | 14.49 |
| Polyethylene glycol digylcidyl ether 526 or 4600 Da | 1.39 | 1.39 |
| Polyvinyl pyrrolidone 58 kDa | 0.14 | 0.14 |
| Polyethylene glycol 10 kDa | 12.82 | 12.82 |
| Deionized water | 67.49 | 67.49 |
| Barium Sulfate | 5.06 | 5.06 |

TABLE 12

Concentrations of Water of the Resultant
Polymer Solutions

| | Sample Composition | |
|---|---|---|
| Resultant Material | A | B |
| Water Content (% w/w) | 60.1 ± 0.6 | 60.1 ± 0.4 |

Example 9

Figure 5:
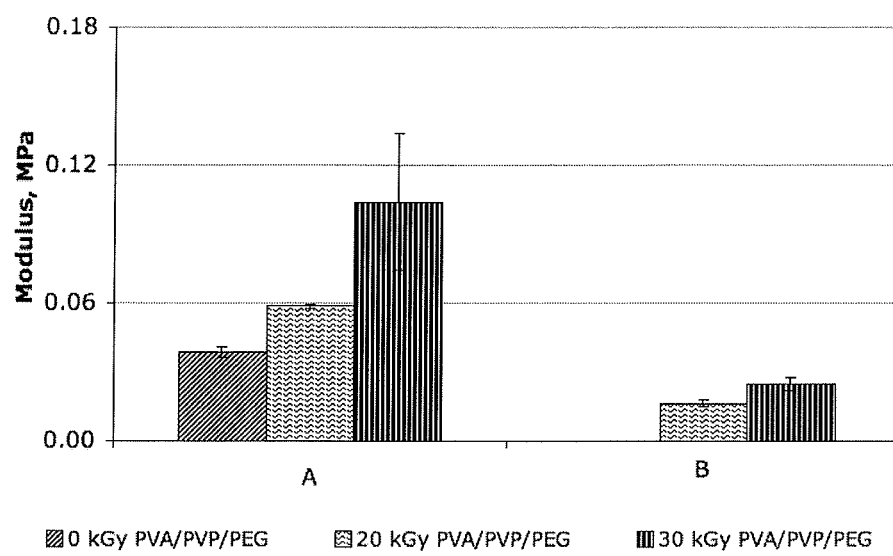
FIG. 5 illustrates the compressive modulus of two formulations of the PVA/PVP/PEG hydrogel irradiated at room temperature with a 10 MeV electron beam to the desired dosages of 20 and 30 kGy.

Electron Beam Irradiation of PVA/PVP/PEG
Hydrogel Compositions Using 10 kDa MW PEG PVA/PVP/PEG hydrogel compositions were prepared generally as described in Example 1 for PVA/PVP/PEG-DGE hydrogels except PEG (MW=10 kDa, supplied by Sigma Aldrich) was used instead of PEG-DGE and no NaOH addition. The resulting hydrogel composition was then irradiated with electron beam at dosages of 20 and 30 kGy. PVA/PVP/PEG hydrogel composition samples were formulated by preparing an aqueous PVA/PVP solution (13.4 and 8.9% w/w) by mixing PVA ((Mowiol 28-99: 145 kDa; 99-99.8 mol % hydrolyzed) supplied by Sigma Aldrich), PVP (C-30; MW=58,000 Da), Barium Sulfate (1-10 μm) and deionized water in a sealed glass bottle and heating to 121° C. for 30 minutes in an autoclave. The ratio of PVA to PVP was 99:1. A 4% to 15% concentration of barium sulfate in the resultant hydrogel composition was sufficient to be radiopaque for hydrogels. The addition of barium sulfate is an optional step. Solutions were then stored at 75° C. in a water bath, the solution was maintained at 75° C.±5° C. during the addition of PEG (MW=10 kDa, supplied by Sigma Aldrich). The initial concentration ranges of the components of the precursor polymer composition are summarized in Table 13. Mechanical test specimens were molded and tested as described in Example 1, compressive moduli of these PVA/PVP/PEG hydrogels with differing dosages are shown in FIG. 5.

TABLE 13

Concentration of Components of the Resultant Electron Beamed PVA/PVP/PEG Hydrogel Composition

| Material | Sample Composition (% w/w) | |
|---|---|---|
| | A | B |
| Polyvinyl alcohol 145 kDa | 13.4 | 8.9 |
| Polyethylene glycol 10 kDa | 11.9 | 7.9 |
| Polyvinyl pyrrolidone 58 kDa | 0.1 | 0.1 |
| Deionized water | 69.9 | 80 |
| Barium Sulfate | 4.7 | 3.1 |

Example 10

Figure 6:
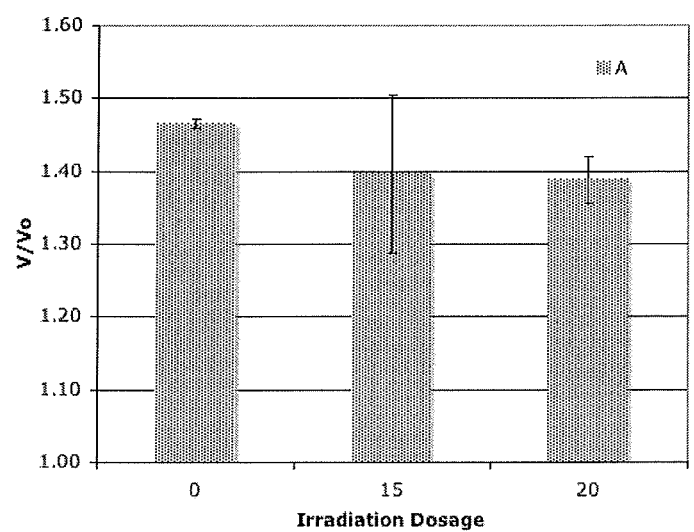
FIG. 6 illustrates the swelling, in a PEG solution with the osmotic pressure of 0.16 MPa, of a formulation of the PVA/PVP/PEG hydrogel irradiated at room temperature with a 10 MeV electron beam to the desired dosages of 15 and 20 kGy.

Electron Beam Irradiation of PVA/PVP/PEG Hydrogel Compositions Using 4.6 kDa MW PEG PVA/PVP/PEG hydrogel compositions were prepared generally as described in Example 9 for PVA/PVP/PEG-DGE hydrogels except the resulting hydrogel composition was then irradiated with electron beam at dosages of 15 and 20 kGy. PVA/PVP/PEG hydrogel composition samples were formulated by preparing an aqueous PVA/PVP solution (14.8 w/w) by mixing PVA ((Mowiol 28-99: 145 kDa; 99-99.8 mol % hydrolyzed) supplied by Sigma Aldrich), PVP (C-30; MW=58,000 Da), Barium Sulfate (1-10 μm) and deionized water in a sealed glass bottle and heating to 121° C. for 30 minutes in an autoclave. The ratio of PVA to PVP was 99:1. A 4% to 15% concentration of barium sulfate in the resultant hydrogel composition was sufficient to make the hydrogels radiopaque. The addition of barium sulfate is an optional step. Solutions were then stored at 75° C. in a water bath, the solution was maintained at 75° C.±5° C. during the addition of PEG (MW=4.6 kDa, supplied by Sigma Aldrich). The initial concentration ranges of the components of the precursor polymer composition are summarized in Table 14. The swelling ratio of the resultant PVA/PVP/PEG hydrogel compositions was tested as in Example 3, this is shown in FIG. 6.

TABLE 14

Concentration of Components of the Resultant Electron Beamed PVA/PVP/PEG Hydrogel Composition

| Material | Sample Composition (% w/w) A |
|---|---|
| Polyvinyl alcohol 145 kDa | 14.8 |
| Polyethylene glycol 4.6 kDa | 13.1 |
| Polyvinyl pyrrolidone 58 kDa | 0.1 |
| Deionized water | 65.0 |
| Barium Sulfate | 7.0 |

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and scope of the invention, and all such variations are intended to be included within the scope of the following claims.

The invention claimed is:

1. An injectable hydrogel composition comprising:
water; and
poly(vinyl alcohol) chemically cross-linked with a second polymer to form a cross-linked resin, wherein the second polymer is selected from the group consisting of: a polyhydric alcohol compound, a polyvalent epoxy compound, a polyvalent amine compound, a dialdehyde compound, a diisocyanate compound, and mixtures thereof,
wherein the cross-linked resin has a degree of chemical cross-linking of from about 0.0001 mol/mL to about 0.002 mol/mL, wherein the hydrogel is flowable when heated above its melting point, and wherein the hydrogel composition exhibits a swelling value of from about 1.033 to about 1.79 in a 0.16 MPa osmotic solution.

2. The hydrogel composition of claim 1 wherein the poly (vinyl alcohol) is present in the composition at a concentration of from about 14% (w/w) to about 21% (w/w).

3. The hydrogel composition of claim 1 wherein the second polymer is a polyvalent epoxy compound.

4. The hydrogel composition of claim 3, wherein the polyvalent epoxy compound is poly(ethylene glycol) diglycidyl ether.

5. The hydrogel composition of claim 3 wherein the poly (ethylene glycol) diglycidyl ether is present in the composition at a concentration of from about 6% (w/w) to about 40% (w/w).

6. The hydrogel composition of claim 1 further comprising polyvinyl pyrrolidone.

7. The hydrogel composition of claim 6 wherein the poly (vinyl pyrrolidone) is present in the composition at a concentration of from about 0.14% (w/w) to about 0.22% (w/w).

8. The hydrogel composition of claim 4 wherein the poly (ethylene glycol) diglycidyl ether has a molecular weight of from about 526 Da to about 4600 Da.

9. The hydrogel composition of claim 1 further comprising an imaging agent.

10. The hydrogel composition of claim 9, where the imaging agent is barium sulfate.

11. The hydrogel composition of claim 1 wherein the composition exhibits a swelling volume change of about 11% to about 17% in a 0.16 MPa osmotic solution.

12. The hydrogel composition of claim 1 wherein the composition has a viscosity of from about 11 Pa*s to about 77 Pa*s at a temperature of 95° C.

13. The hydrogel composition of claim 8 wherein the poly (ethylene glycol) diglycidyl has a molecular weight of about 526 Da and the composition has an elastic modulus of from about 0.03 MPa to about 1.8 MPa.

14. The hydrogel composition of claim 1 wherein the cross-linked resin has a degree of cross-linking of from about 0.0007 mol/mL to about 0.0011 mol/mL.

15. The hydrogel composition of claim 14 wherein the cross-linked resin has a degree of cross-linking of about 0.0009 mol/mL+/−0.0002 mol/mL.

16. The hydrogel composition of claim 1 wherein the second polymer is poly(ethylene glycol) at a concentration of from about 12% (w/w) to about 18% (w/w).

17. The hydrogel composition of claim 16 further comprising an imaging agent.

18. The hydrogel composition of claim 17 wherein the imaging agent is barium sulfate.

19. The hydrogel composition of claim 5 wherein the poly(ethylene glycol) diglycidyl ether is present in the composition at a concentration of from about 19% (w/w) to about 38% (w/w).

20. The hydrogel composition of claim 19 wherein the poly(ethylene glycol) diglycidyl ether is present in the composition at a concentration of from about 27% (w/w) to about 38% (w/w).

21. The hydrogel composition of claim 1 wherein hydrogel composition exhibits a swelling volume change of about 11% to about 17% in a 0.16 MPa osmotic solution.

* * * * *

UNITED STATES PATENT AND TRADEMARK OFFICE
CERTIFICATE OF CORRECTION

PATENT NO.         : 8,617,519 B2                                   Page 1 of 1
APPLICATION NO.    : 13/177613
DATED              : December 31, 2013
INVENTOR(S)        : Valerie R. Binetti et al.

It is certified that error appears in the above-identified patent and that said Letters Patent is hereby corrected as shown below:

Title Page, Item (73) should read as follows:

item (73) Assignee: DePuy Synthes Products, LLC, Raynham, MA (US)
                       Drexel University, Philadelphia, PA (US)

Signed and Sealed this
Twenty-fourth Day of June, 2014

Michelle K. Lee
*Deputy Director of the United States Patent and Trademark Office*